US005669936A

United States Patent [19]
Lazarus

[11] Patent Number: 5,669,936
[45] Date of Patent: *Sep. 23, 1997

[54] ENDOVASCULAR GRAFTING SYSTEM AND METHOD FOR USE THEREWITH

[75] Inventor: Harrison M. Lazarus, Salt Lake City, Utah

[73] Assignee: Endovascular Technologies, Inc., Menlo Park, Calif.

[*] Notice: The term of this patent shall not extend beyond the expiration date of Pat. No. 4,787,899.

[21] Appl. No.: 395,157

[22] Filed: Feb. 27, 1995

Related U.S. Application Data

[63] Continuation of Ser. No. 103,442, Aug. 6, 1993, abandoned, which is a continuation of Ser. No. 553,530, Jul. 13, 1990, Pat. No. 5,275,622, which is a continuation-in-part of Ser. No. 166,093, Mar. 9, 1988, Pat. No. 5,104,399, which is a continuation-in-part of Ser. No. 940,907, Dec. 10, 1986, Pat. No. 4,787,899, which is a continuation of Ser. No. 559,935, Dec. 9, 1993, abandoned.

[51] Int. Cl.⁶ .............................. A61F 2/06; A61M 29/00
[52] U.S. Cl. .............................. 623/1; 623/12; 606/195
[58] Field of Search .................... 623/1, 11, 12; 604/96; 606/191–198

[56] References Cited

U.S. PATENT DOCUMENTS

| 3,878,565 | 4/1975 | Sauvage | 623/1 |
|---|---|---|---|
| 3,882,852 | 5/1975 | Sinnreich | 604/96 X |
| 3,890,976 | 6/1975 | Bazell et al. | 604/96 X |
| 4,140,126 | 2/1979 | Choudhury | 623/1 |
| 4,141,364 | 2/1979 | Schultze | 604/96 |
| 4,276,874 | 7/1981 | Wolvek et al. | 604/96 |
| 4,560,374 | 12/1985 | Hammerslag | 604/49 |
| 4,655,771 | 4/1987 | Wallstén | 623/1 |
| 4,787,899 | 11/1988 | Lazarus | 623/1 |
| 4,954,126 | 9/1990 | Wallstén | 623/1 X |
| 5,104,399 | 4/1992 | Lazarus | 623/1 |

FOREIGN PATENT DOCUMENTS

| 1217402 A | 3/1986 | U.S.S.R. |
| 1318235 A1 | 6/1987 | U.S.S.R. |
| 1389778 A2 | 4/1988 | U.S.S.R. |
| 1457921 A1 | 2/1989 | U.S.S.R. |
| 1482714 A2 | 5/1989 | U.S.S.R. |

*Primary Examiner*—Debra S. Brittingham
*Attorney, Agent, or Firm*—Fulwider Patton Lee & Utecht

[57] ABSTRACT

Endovascular grafting system having a capsule catheter comprising a flexible elongate tubular member having proximal and distal extremities and a capsule mounted on the distal extremity of the tubular member. The capsule is generally cylindrical in shape and is formed of a helical wrap of a metal ribbon. The wraps are bonded into a unitary capsule permitting bending of said unitary capsule. A graft is disposed within the capsule. The graft is comprised of a tubular member having proximal and distal ends. Hooks are secured to the proximal and distal ends of the tubular member and face in a direction outwardly towards the inner wall of the capsule. A push rod is disposed within the capsule catheter and engages the graft whereby upon relative movement between the push rod and the capsule catheter, the graft can be forced out of the capsule.

24 Claims, 5 Drawing Sheets

ENDOVASCULAR GRAFTING SYSTEM AND METHOD FOR USE THEREWITH

This is a continuation of application Ser. No. 08/103,442, filed on Aug. 6, 1993, now abandoned, which is a continuation of application Ser. No. 07/553,530, filed on Jul. 13, 1990, now U.S. Pat. No. 5,275,622, which is a continuation-in-part of application Ser. No. 07/166,093, filed on Mar. 9, 1988, now U.S. Pat. No. 5,104,399, which is a continuation-in-part of application Ser. No. 06/940,907, filed on Dec. 10, 1986, now U.S. Pat. No. 4,787,899, which is a continuation of application Ser. No. 06/559,935, filed on Dec. 9, 1983, now abandoned.

This application relates to endovascular grafting apparatus, system and method and devices for use therewith.

The state of the art is described in the background of the invention in U.S. Pat. No. 4,787,899.

In general, it is an object of the present invention to provide an endovascular grafting apparatus, system and method and devices for use therewith which overcome the disadvantages of the prior art apparatus, systems and devices.

Another object of the invention is to provide an apparatus and system of the above character which utilizes a pusher rod assembly which is constrained so that relatively great forces can be applied by the pusher rod assembly.

Another object of the invention is to provide an apparatus and system of the above character in which the capsule is flexible so that it can negotiate bends in the vessels of a patient.

Another object of the invention to provide a grafting apparatus and system which utilizes a flexible capsule which can contain a graft with hook-like elements without any danger of the hook-like elements penetrating the capsule.

Another object of the invention is to provide an apparatus and system of the above character in which the graft automatically springs into an open or expanded position when it is released from the capsule.

Another object of the invention is to provide an apparatus, system and method of the above character in which a pushing force is applied to the distal extremity of the balloon for advancing a graft out of the capsule.

Another object of the invention is to provide an apparatus and system of the above character in which a fixed wire or an over-the-wire guide wire system can be used.

Another object of the invention is to provide an apparatus and system of the above character in which the graft can be compressed to a very small size in a flexible capsule.

Additional objects and features of the invention will appear in the following description in conjunction with the accompanying drawings.

In general, the endovascular grafting system is comprised of a capsule catheter having a flexible elongate tubular member with proximal and distal extremities and a capsule mounted on the distal extremity of the tubular member. The capsule is generally cylindrical in shape and is formed of a helical wrap of a metal ribbon. Means is provided for bonding said wraps into a unitary capsule while permitting bending of said unitary capsule. A graft is disposed within the capsule. The graft is comprised of a tubular member having proximal and distal ends. Hook-like attachment means is secured to the proximal and distal ends of the tubular member and face in a direction outwardly towards the inner wall of the capsule. Push rod means is disposed within the capsule catheter and engages the graft whereby upon relative movement between the push rod means and the capsule catheter, the graft can be forced out of the capsule.

More in particular, the endovascular grafting apparatus and system 11 and the devices for use therein are shown in FIGS. 1–10. This apparatus and system 11 includes a capsule catheter 12 (see FIG. 2) which consists of a flexible elongate tubular member 16 formed of a suitable plastic material such as Nylon of a suitable length as, for example, 40 to 100 centimeters and preferably approximately 43 centimeters for the abdominal aortic artery and approximately 70 centimeters for the thoracic aortic artery. The tubular member 16 can have a suitable size such as an outside diameter of 0.187 inches and an inside diameter of 0.125 inches. The tubular member 16 can be produced in a certain color such as blue. In order to make it radiopaque under x-rays, the flexible tubular member 16 is loaded with a suitable radiopaque material such as bismuth subcarbonate or barium sulfate. By way of example, the flexible elongate member 16 can be compounded with approximately 20% of the radiopaque material by weight.

Figures 1, 2:
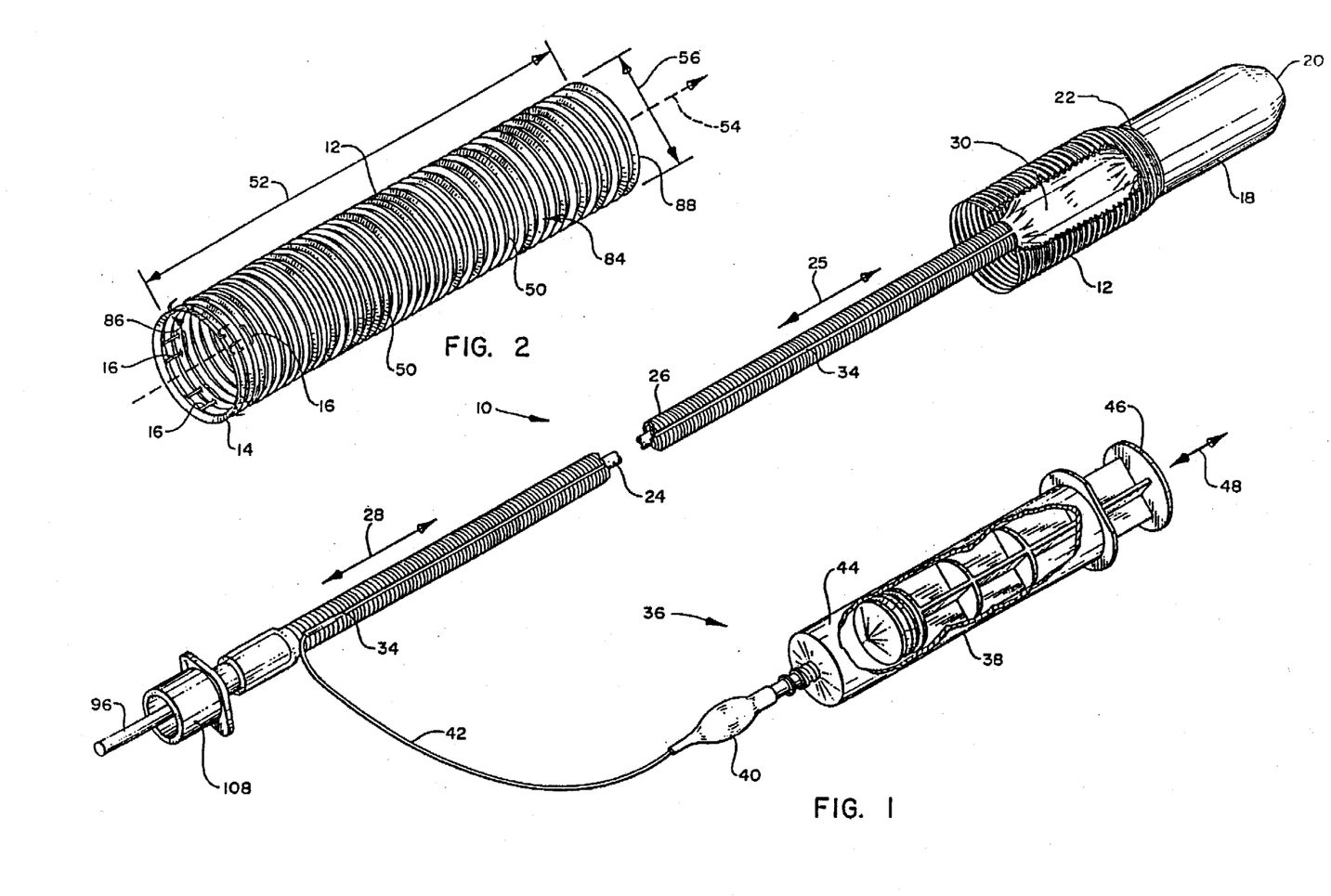
FIG. 1 is an isometric view of an endovascular grafting apparatus and system incorporating the present invention.
FIG. 2 is a side elevational view partially in cross section of a capsule catheter incorporating the present invention.
Figure 1:
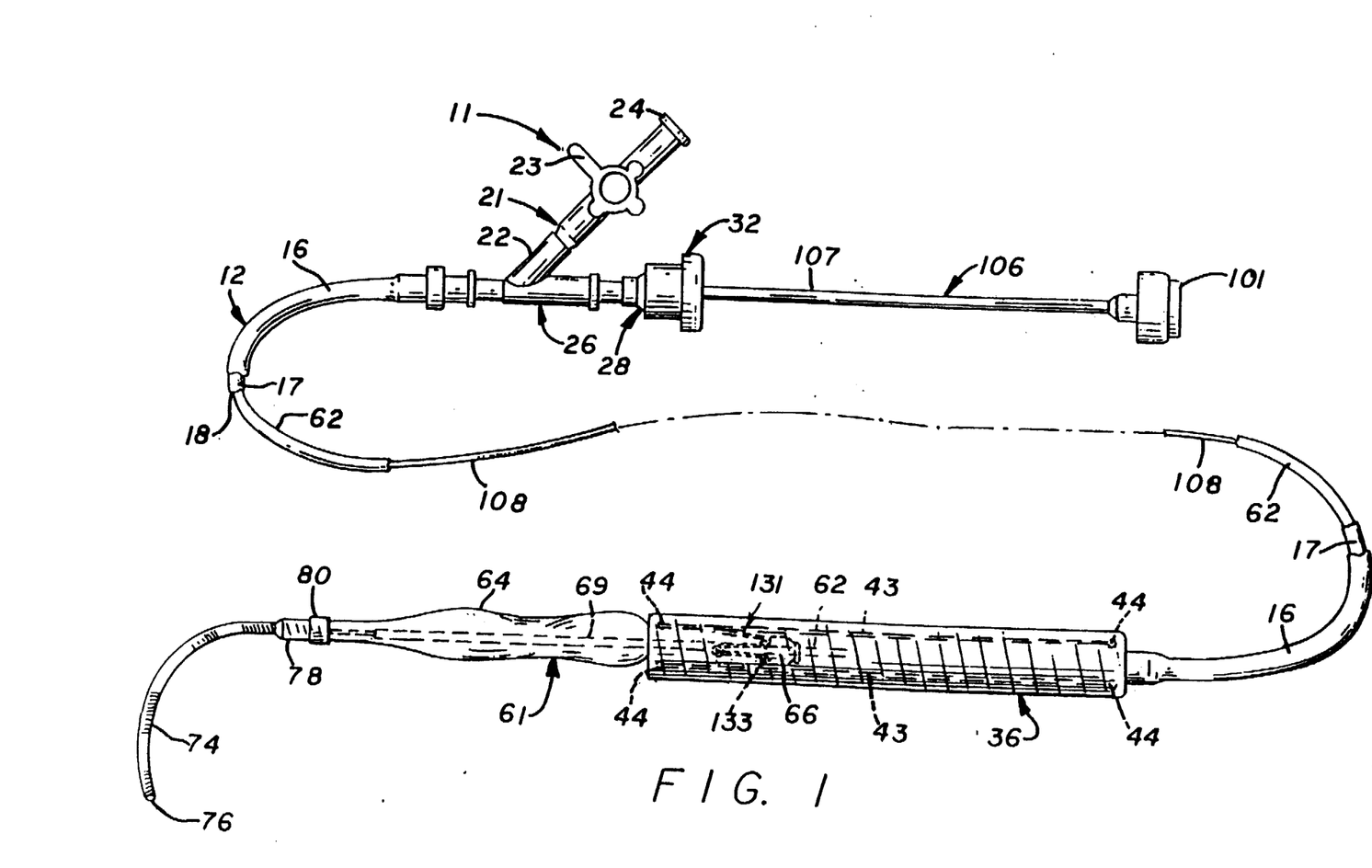
Figure 2:
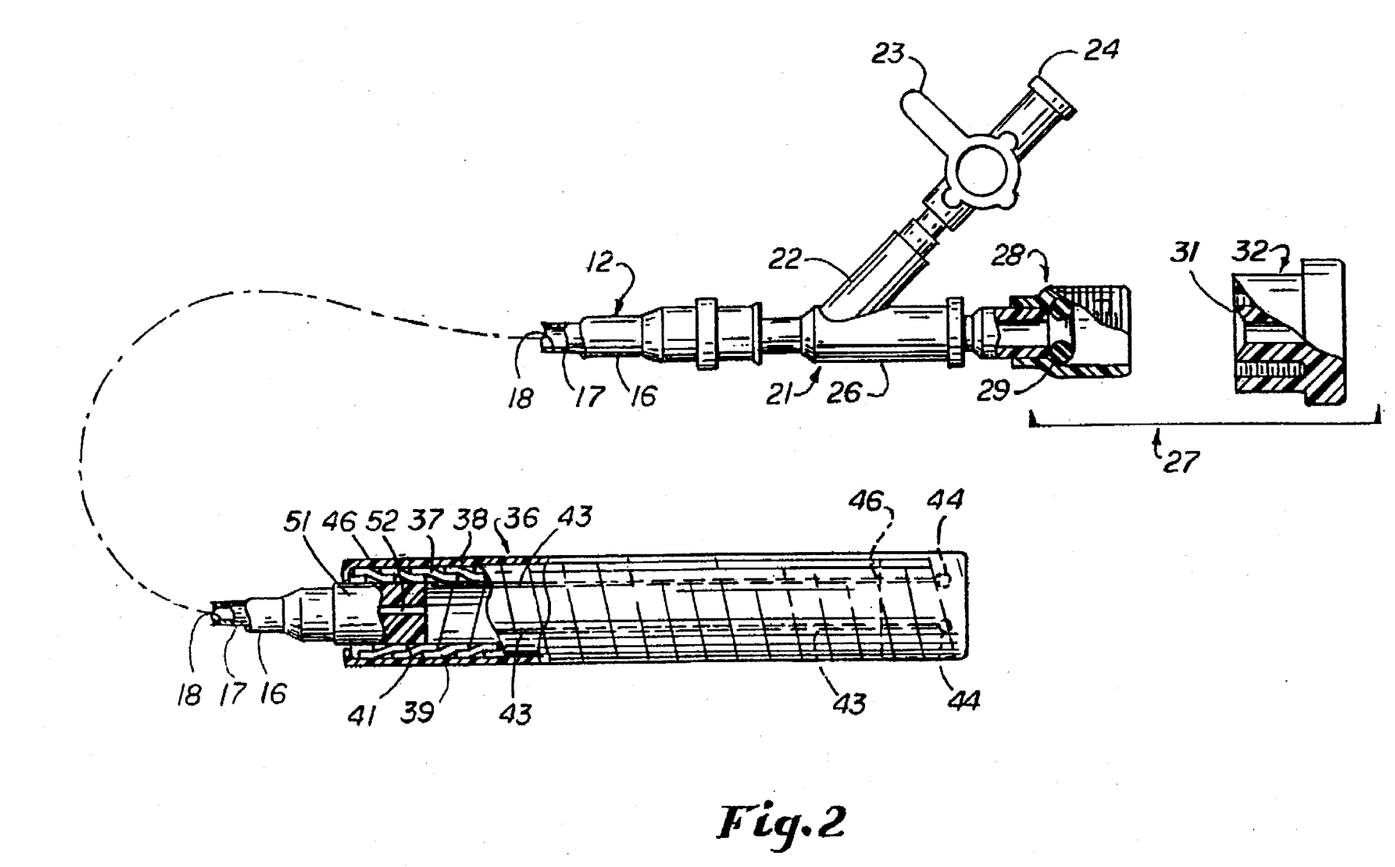

An inner liner 17 is provided which is mounted within the tubular member 16. The liner 17 is sized so that it will fit within the tubular member 16. The liner is preferably formed of a lubricious material such as Tefzel (ethylene tetrafluoroethylene) or Teflon FEP (flourinated ethylene polypropylene). It can have an inside diameter of 0.085 inches and an outside diameter of 0.125 inches and a length as, for example, 41 centimeters which is slightly less than that of the tubular member 16. If desired, the inside diameter of the liner 17 can be in the range of 0.075 to 0.120 inches. The liner 17 is provided with a lumen 18 which extends the length thereof. The liner 17 reduces the inside diameter of the lumen 18 for a purpose hereinafter described. The liner 17 is made of a radiation stable material so that the catheter can be radiation sterilized. Tefzel, or Teflon FEP, which is a polymer is such a radiation sterilizable material. The inner liner 17 also serves to provide additional columnar strength to the catheter 12.

A wye adapter 21 is secured to the proximal extremity of the flexible tubular member 16. The side arm 22 of the adapter 21 has a stop cock 23 mounted therein which is movable between open and closed positions. The stop cock 23 is provided with a Luer fitting 24 which is adapted to be secured to a syringe which can be utilized for injecting a dye, or medications such as a vasodilator. The central arm 26 of the adapter 21 is connected to a Touhy Borst adapter 27 and includes a female part 28 that carries an O-ring 29 which is adapted to be engaged by a protrusion 31 forming a part of the male part 32.

The capsule catheter 12 has a capsule 36 incorporating the present invention mounted on the distal extremity of the flexible elongate tubular member 16. The capsule 36 when used in humans has a diameter ranging from 4 to 8 millimeters. The flexible elongate tubular member 16 which also serves as a shaft for advancing the capsule 36 as hereinafter described and should have a diameter which is less than that of the capsule and therefore has an outside diameter ranging from 3 to 7 millimeters.

The capsule 36 is a composite structure and is formed of an inner layer 37 and an outer layer 38. The inner layer 37 is formed of a stainless steel ribbon 39 with the ribbon having a width of 0.150 inches and a thickness ranging from 0.002 to 0.004 inches and preferably approximately 0.003 inches. The ribbon is spiral wound on a mandrel (not shown) so that each wrap of the ribbon overlaps the preceding wrap by approximately 30 to 50% of the width of the ribbon. Viewing the capsule 36 from the left hand end, the ribbon is wrapped in a clockwise or counterclockwise direction so that the edges 41 face distally or in the direction which is toward the right as shown in FIG. 2 for a purpose hereinafter described. By winding the ribbon 37 at high tension, it is possible to deform it over the adjacent wrap which contributes to the flexibility of the capsule and also at the same time makes it possible to provide a capsule having a low profile. The stainless steel for the ribbon 39 can be of any suitable type, however, it has been found that it is desirable to select a stainless steel which can be heat treated. This enables one to wind the capsule with the ribbon in a ductile state and heat treat the capsule after winding to obtain a spring-like temper. One such stainless steel is 17-7 PH supplied by Brown Metals Company of Santa Fe Springs, Calif.

In order to prevent elongation of the capsule 36 and also to prevent one wrap separating from another of the inner layer 37, a plurality of elongate flexible strands 43 are provided which extend from one end to the other of the capsule. It has been found that the use of four strands has been sufficient with the strands being spaced apart circumferentially by 90°. The strands 43 can be formed of a suitable material such as a Kevlar aramid fiber, 195 denier. These four strands 43 are bonded to the proximal and distal extremities of the capsule by a suitable adhesive such as a cyanoacrylate ester at points 44. The outer layer 38 which overlies the strands 43 and the wrapped ribbon inner layer 37 is in the form of a jacket formed of a suitable material such as heat shrinkable polyethylene. This jacket can have a wall thickness ranging from 0.001 to 0.006 inches and preferably a thickness of approximately 0.004 inches. The polyethylene jacket which forms the outer layer 38 serves to contain the Kevlar strands 43 in close proximity to the inner layers 37 and also serves to prevent elongation of the capsule 36 while permitting the capsule to bend during use as hereinafter described. The outer layer or jacket 38 serves also to provide a smooth surface for the exterior of the capsule 36 by enclosing the edges 41 of the wraps of ribbon 39. In addition, the proximal and distal extremities of the capsule 36 are bonded together by a solder in the regions 46 as indicated in FIG. 2. The solder can be of a suitable type, such as a tin silver solder comprised of 95% tin and 5% silver. When constructed in this manner, the capsule 36 can have an inside diameter of 0.175 inches to 0.300 inches with a nominal wall thickness of 0.0012 inches.

The capsule 36 is secured to the distal extremity of the flexible elongate tubular member 16 by a capsule adapter 51 of a suitable material such as a polycarbonate. The capsule adapter 51 is secured in the proximal extremity of the capsule 36 by suitable means, as a press fit or alternatively, in addition, by the use of a suitable adhesive such as a cyanoacrylate ester. The other extremity of the capsule adapter 51 is also mounted in a suitable manner such as by a cyanoacrylate ester adhesive to the distal extremity of the flexible elongate tubular member 16. The capsule adapter 51 is provided with a hole 52 of a suitable diameter such as 1/16th of an inch.

The capsule 36 made in accordance with the present invention has a number of desirable features. It is particularly desirable because it is flexible and can be bent through an angle of 70° to 120° in a length of 8–20 centimeters. In order to prevent hangups on the inside edges 41 of the ribbon, the inside edges are rounded and polished, preventing damage to capsule contents during ejection as hereinafter described. The Kevlar strands 43, which are also contained by the outer jacket or layer 38, serve to maintain the wrap, prevent stretching or elongation and prevent discontinuities from being formed in the capsule during use of the same. In addition, the Kevlar strands prevent the capsule from being flexed beyond a predetermined angle, as, for example, 120°.

Thus, it can be seen that a capsule 36 has been provided which is very flexible, yet is still very hard and has great strength which inhibits crushing or collapsing while being bent or flexed. In other words, it is kink resistant. It is also puncture proof due to the use of the metal ribbon 37. The capsule 36 is semi-radiopaque and is radiation sterilizable.

Figures 3, 4:
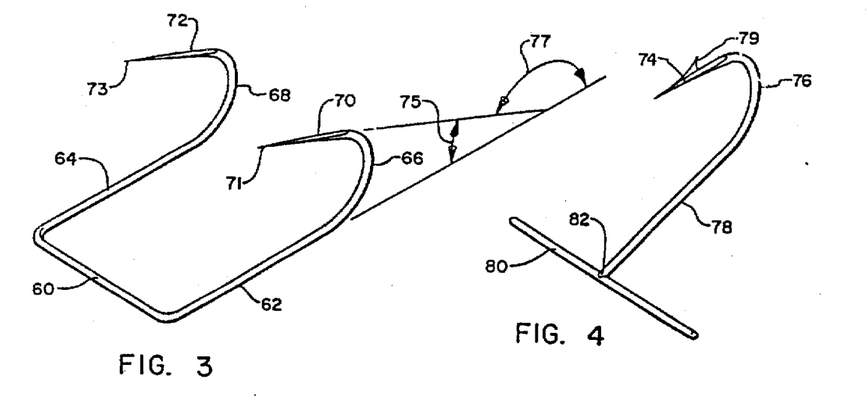
FIG. 3 is a side elevational view partially in cross section showing a balloon catheter assembly incorporating the present invention.
FIG. 4 is a partial side elevational view in cross section of a portion of an alternative balloon catheter assembly incorporating the present invention showing the use of a movable pusher button capable of sliding over a limited range.
Figure 3:
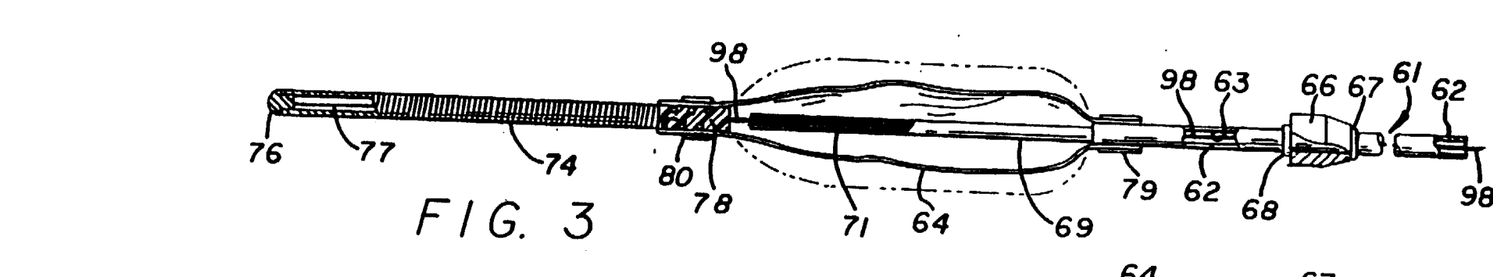
Figure 4:
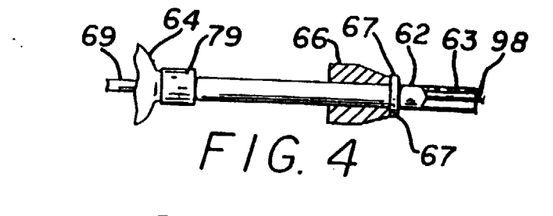

The endovascular grafting apparatus also includes a balloon catheter assembly 61 which consists of a shaft in the form of a flexible elongate element 62 formed of a suitable material such as irradiated polyethylene tubing extruded to a larger diameter of 0.160 inches outside diameter and 0.090 inches inside diameter and then reduced in size by heating and elongating the same to provide an inside diameter of 0.020 inches and an outside diameter of 0.050 inches. However, the inside diameter can range from 0.015 to 0.025 inches and the outside diameter can range from 0.035 to 0.065 inches for a single lumen balloon catheter assembly. The single balloon inflation lumen 63 extends the length of the catheter. The catheter can have a suitable length as, for example, 50 to 130 centimeters. The lumen 63 can also serve as an injectate lumen and a pusher wire lumen as hereinafter described.

A separate balloon 64 formed of suitable material such as polyethylene is secured to the distal extremity of the flexible elongate member 62 in a manner hereinafter described. A pusher button 66 is provided which is formed of a suitable material such as 300 series stainless steel. The pusher button 66 can have a diameter ranging from 0.120 inches to 0.200 inches and preferably an outside diameter of approximately 0.140 inches. Stainless steel is utilized to achieve radiopacity.

The pusher button 66 is mounted on a fixed position on the catheter shaft 62 and is spaced a predetermined distance from the proximal extremity of the balloon 64 as, for example, a distance of 2 to 3 centimeters. The pusher button 66 is retained in this position longitudinally of the shaft 62 by annular bulbs 67 and 68 which are formed by localized heating in those areas of the shaft 62 which causes it to expand radially in an attempt to achieve its original size to trap the pusher button 66 in that position on the shaft 62. Thus, it can be seen that the pusher button 66 can be mechanically trapped in place without the use of an adhesive and without changing the size of the lumen 63 which extends therethrough.

An alternative embodiment in which the pusher button 66 is movable between the proximal extremity of the balloon 64 and a single bulb 67 is shown in FIG. 4.

A small stainless steel tube 69 is disposed within the balloon 64 and has its proximal extremity seated within the distal extremity of the shaft or flexible elongate member 62. The tube 69 has a suitable inside diameter such as 0.022 inches, an outside diameter of 0.032 inches and a suitable length as, for example, 7.5 centimeters. As can be seen from FIG. 3, the tube 69 extends through the balloon 64 and terminates in the distal extremity of the balloon. The proximal extremity of the tube 69 is flared slightly so that it is firmly retained within the shaft 62 when the proximal extremity of the balloon is fused to the shaft 62 by the use of heat. The tube 69 serves to provide stiffness to the balloon 64 of the balloon catheter assembly 61 and is provided with a lumen 71 extending therethrough through which a fluid such as a gas or liquid can be introduced from the lumen 63 into the lumen 71 to inflate the balloon and to thereafter deflate the balloon 64 by withdrawing the gas or liquid. The balloon 64 can vary in diameter from 12 to 35 millimeters in diameter and can have a wall thickness ranging from 0.001 and 0.005 inches. The polyethylene utilized for the balloon is irradiated to achieve an appropriate balloon size. One balloon made in accordance with the present invention had an outside diameter of 16 millimeters and had a wall thickness of approximately 0.003 inches. In addition, the balloon when deflated is twisted into a helix and heated so as to provide it with a memory which facilitates its introduction into a vessel of a patient as hereinafter described.

A very flexible guide wire 74 is secured to the distal extremity of the balloon 64. The guide wire can have a suitable diameter such as 0.052 inches in outside diameter and can have a suitable length, as for example, 7 centimeters. The guide wire 74 can be a spring formed from wire having a suitable diameter such as 0.009 inches so that it will be radiopaque and thus readily observable under x-rays when being used. The guide wire is provided with a rounded tip 76 which can be formed from a suitable material such as a tin silver solder of 95% tin and 5% silver. The solder tip 76 has bonded therein the distal extremity of a safety ribbon 77 which extends towards the proximal extremity of the spring guide wire 74 and is secured to the proximal extremity thereof by suitable means such as the same tin silver solder hereinbefore described. The guide wire 74 can range in diameter from 0.036 inches to 0.060 inches. The ribbon 77 can be formed of a suitable material such as stainless steel and have a thickness of 0.003 inches and a width of 0.010 inches.

As can be seen from FIG. 3, the proximal extremity of the spring guide wire 74 has been stretched longitudinally beyond the yield point so that there is a space or interstice between each turn of the wire forming the proximal extremity of the spring. A plug 78 of a non-irradiated polyethylene is placed within the proximal extremity of the spring guide wire 74 but remote from the distal extremity of the tube 69. The plug 78 and the distal extremity of the balloon 64 are then heated to cause the non-irradiated polyethylene to melt and flow into the interstices of the stretched spring 74 to bond the spring 74 to the distal extremity of the balloon 64 and to seal the distal extremity of the balloon so that gas cannot escape therefrom.

The guide wire 74 is easily observed using x-rays due to its width and stainless steel composition. Since the pusher button 66 is also formed of stainless steel, it also is an easy marker to follow. The pusher button 66 and guide wire 74 help indicate the position of the balloon 64 because the balloon 64 is positioned between the pusher button 66 and the guide wire 74. The balloon 64 itself can be observed under x-rays because the blood in the patient's vessel is more opaque than the gas used for inflating the balloon. However, increased visibility of the balloon 64 can be obtained by inflating the balloon 64 with a diluted radiopaque contrast solution. In addition, if desired as shown in FIG. 3, two radiopaque bands 79 and 80 of a suitable material such as platinum or a platinum tungsten alloy can be placed on the proximal and distal extremities or necked-down portions of the balloon 64 to aid in ascertaining the position of the balloon 64.

It should be appreciated that although a separate balloon 64 has been provided, if desired, an integral balloon can be provided which is formed of the same tubing from which the flexible elongate tubular member 62 is made. This can be readily accomplished, as is well known to those skilled in the art, by using an additional radiation dose for the balloon region of the tubing.

Figure 5:
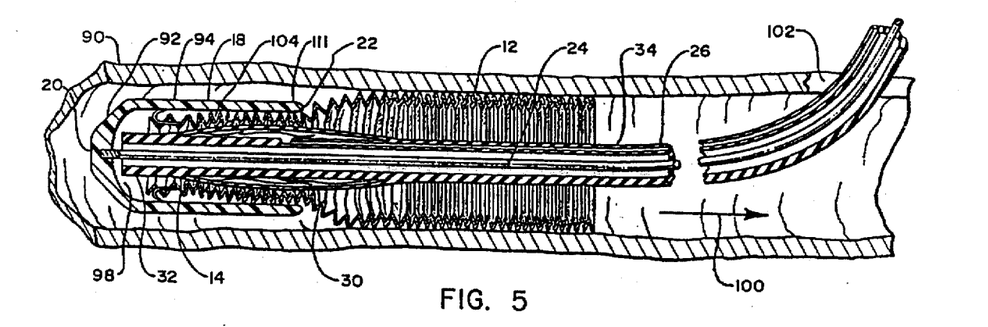
FIG. 5 is a side elevational view partially in cross section of another alternative embodiment of a balloon catheter assembly incorporating the present invention showing the use of a movable guide wire.
Figures 5, 6:
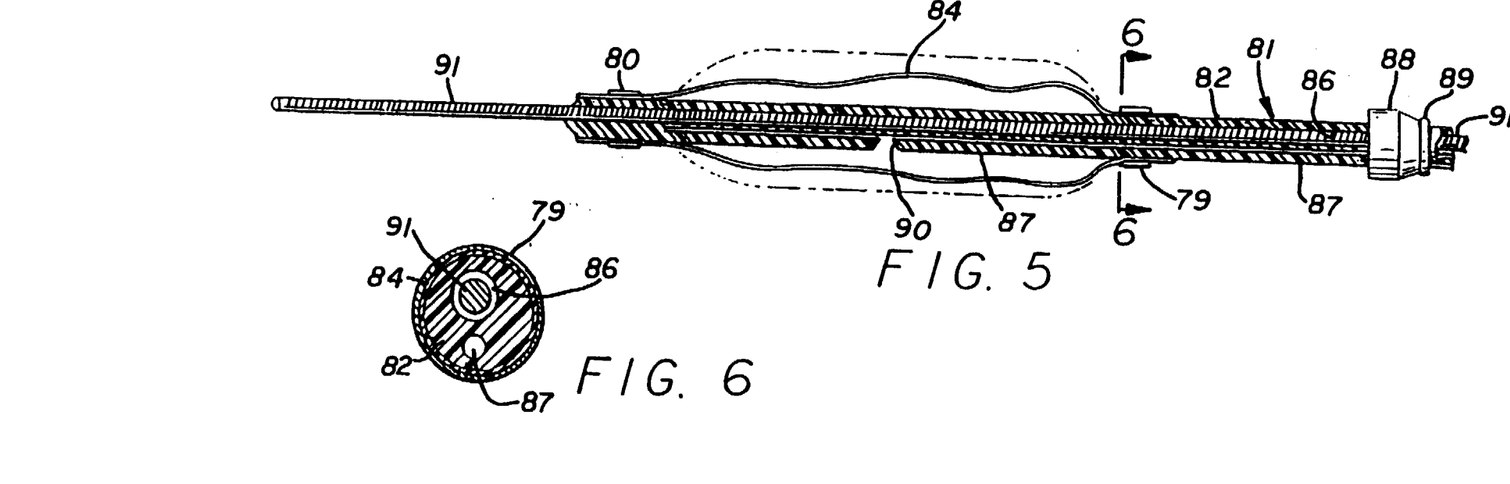
FIG. 6 is a cross sectional view taken along the line 6—6 of FIG. 5.
Figure 6:
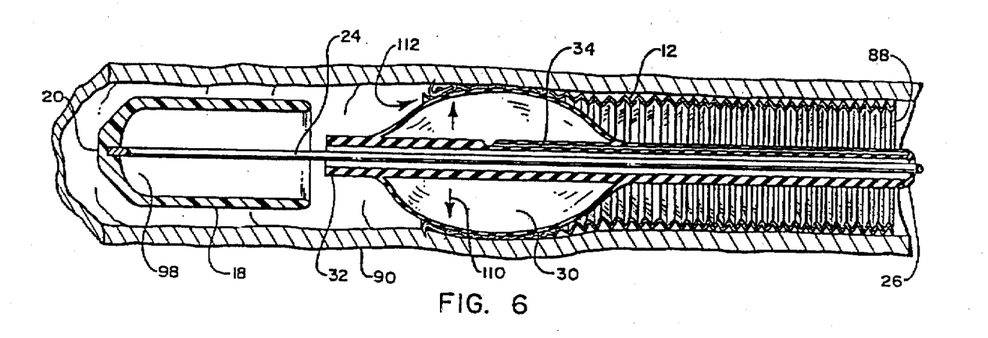

In FIGS. 5 and 6 there is shown an alternative balloon catheter assembly 81 which utilizes a multi-lumen flexible shaft 82 having a balloon 84 secured to the distal extremity of the same. The flexible shaft 82 is provided with a guide wire lumen 86 of a suitable size, as for example, 0.040 inches which extends the entire length of the shaft and through the balloon 84. It is also provided with a balloon inflation lumen 87 of a smaller size such as 0.010 to 0.015 inches which opens through a notched recess 90 into the interior of the balloon 84. The lumen 87 can be connected to a suitable syringe or other device for inflating and deflating the balloon 84. A pusher button 88 is mounted on the shaft 82 which is held in place by a bulb 89 formed on the shaft 82. A conventional guide wire 91 can then be inserted into the lumen 86 of the catheter assembly 81 and utilized in a conventional manner to advance the balloon catheter into tortuous vessels. Thus it can be seen that applicants' balloon catheter assembly 61 can be utilized in an over-the-wire system which is commonly used in angioplasty. The proximal and distal extremities of the balloon 84 can be fused by heat to the shaft 82 so that the balloon 84 can be inflated and deflated. With the guide wire 91 removed the lumen 86 can be used as an injectate lumen.

Figure 7:
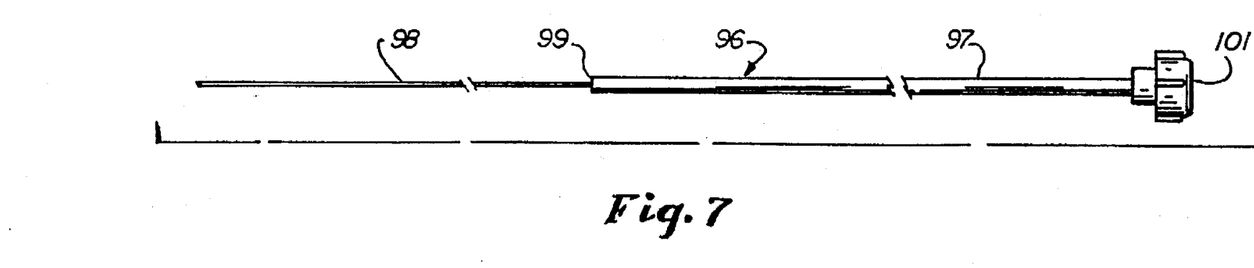
FIG. 7 is a side elevational view partially in cross section of a pusher rod assembly incorporating the present invention.

The endovascular grafting apparatus also includes a pusher rod assembly 96 which is shown in FIG. 7. It consists of a rigid thin wall tube 97 formed of a suitable material such as stainless steel. It has a suitable length as, for example, 21 centimeters and has an outside diameter of 0.065 inches and an inside diameter of 0.053 inches. An elongate solid flexible wire 98 of a suitable diameter as, for example, 0.018 inches is provided which extends centrally into the bore 99 of the tube for the entire length of the rigid tube 97. The wire 98 is secured by suitable means such as an adhesive into a male Luer cap 101 mounted on the proximal end of the tube 97.

The outside of the tube 97 is small enough so that it can slide inside the lumen sleeve 18 of the liner 17 of the catheter 12. The bore 99 of the rigid tube 97 is large enough so that it can receive the balloon catheter shaft 62 with the wire 98 extending into the lumen 63 of the shaft 62. The wire 98 is long enough so that it can extend through the balloon shaft 62 and through the balloon 64 and the tube 69 to engage the plug 78 provided at the distal extremity of the balloon 64. Typically, the pusher rod assembly 96 has a total length of approximately 75 centimeters.

Figures 8, 9:
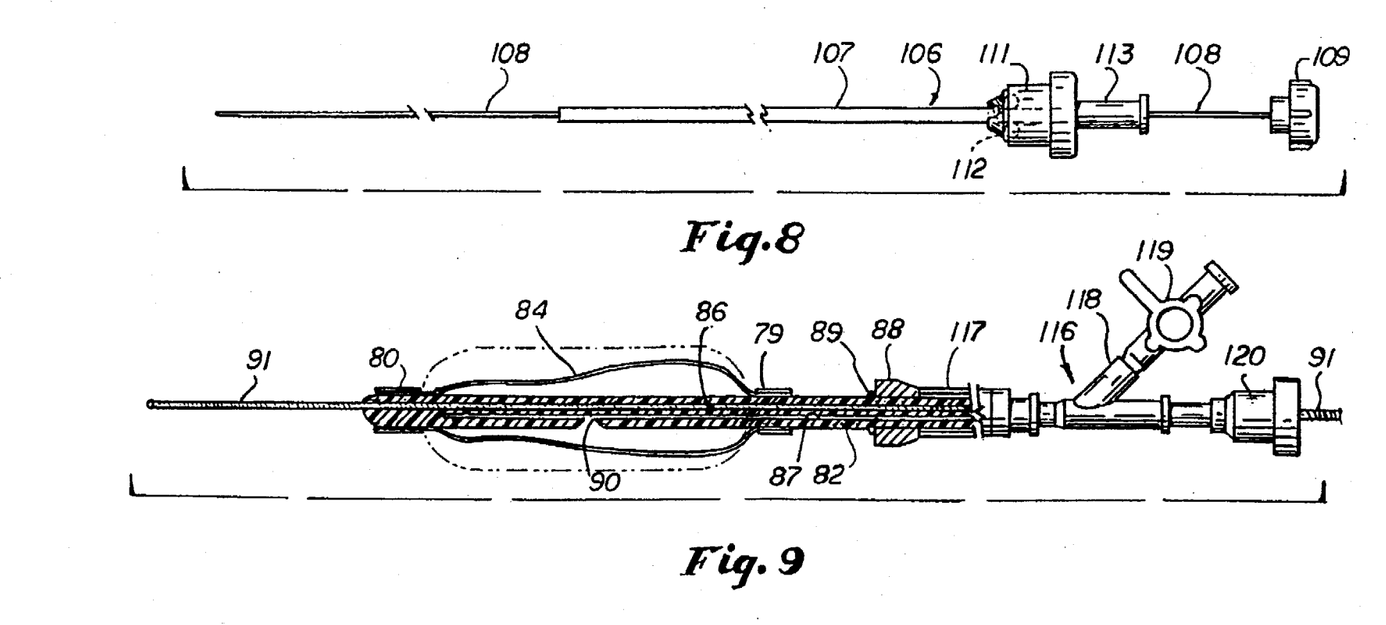
FIG. 8 is a side elevational view partially in cross section of another embodiment of a pusher rod assembly incorporating the present invention.
FIG. 9 is a cross sectional view partially in cross section showing in combination a balloon catheter and a pusher rod assembly and a movable guide wire.

An alternative pusher rod assembly 106 is shown in FIG. 8 and consists of a rigid tube 107 similar to the tube 97 with a 0.018 wire 108 extending into the same and being connected to a male Luer cap 109. A Touhy Borst O-ring adapter 111 is secured to the proximal extremity of the tube 107 and is provided with an O-ring 112. A female Luer fitting 113 is mounted on the Touhy Borst adapter 111. In use of pusher rod assembly 106, the shaft 62 of the balloon catheter assembly 61 is threaded into the tube 106 over the wire 108 and through the o-ring 112. The proximal extremity of the shaft 62 is flared slightly over the o-ring after which the Touhy Borst adapter 111 can be tightened to seal the o-ring 112 around the balloon catheter shaft 62. After certain operations are accomplished as hereinafter described, the male Luer cap 109 and the wire 108 attached thereto can be removed and a syringe (not shown) can be placed on a female Luer adapter 113 to inflate the balloon.

An alternative embodiment of a pusher rod assembly 116 cooperating with the balloon catheter assembly 81 shown in FIG. 5 is shown in FIG. 9. The pusher rod assembly 116 is comprised of a flexible relatively rigid tubular sleeve 117 of stainless steel which has a bore of a diameter to accommodate the shaft 82 of the catheter assembly 81 through which the guide wire 91 extends. A wye adapter 118 is secured to the proximal extremity of the sleeve 117. A stop 119 is mounted in the side arm of the adapter 118 and a Touhy Borst adapter 120 is mounted in the central arm of the adapter 118. The guide wire 91 extends through the guide wire lumen 86 and through the wye adapter 118 and the touhy Borst adapter 120 so that it can be readily engaged by the hand for advancing and retracting the guide wire 91. The balloon 84 can be inflated and deflated through the stop cock 119. By pushing on the adapter 118 a force is applied to the pusher button 88 by the coaxial sleeve 117 for a purpose hereinafter described.

Figures 10, 11, 12, 13, 14, 15:
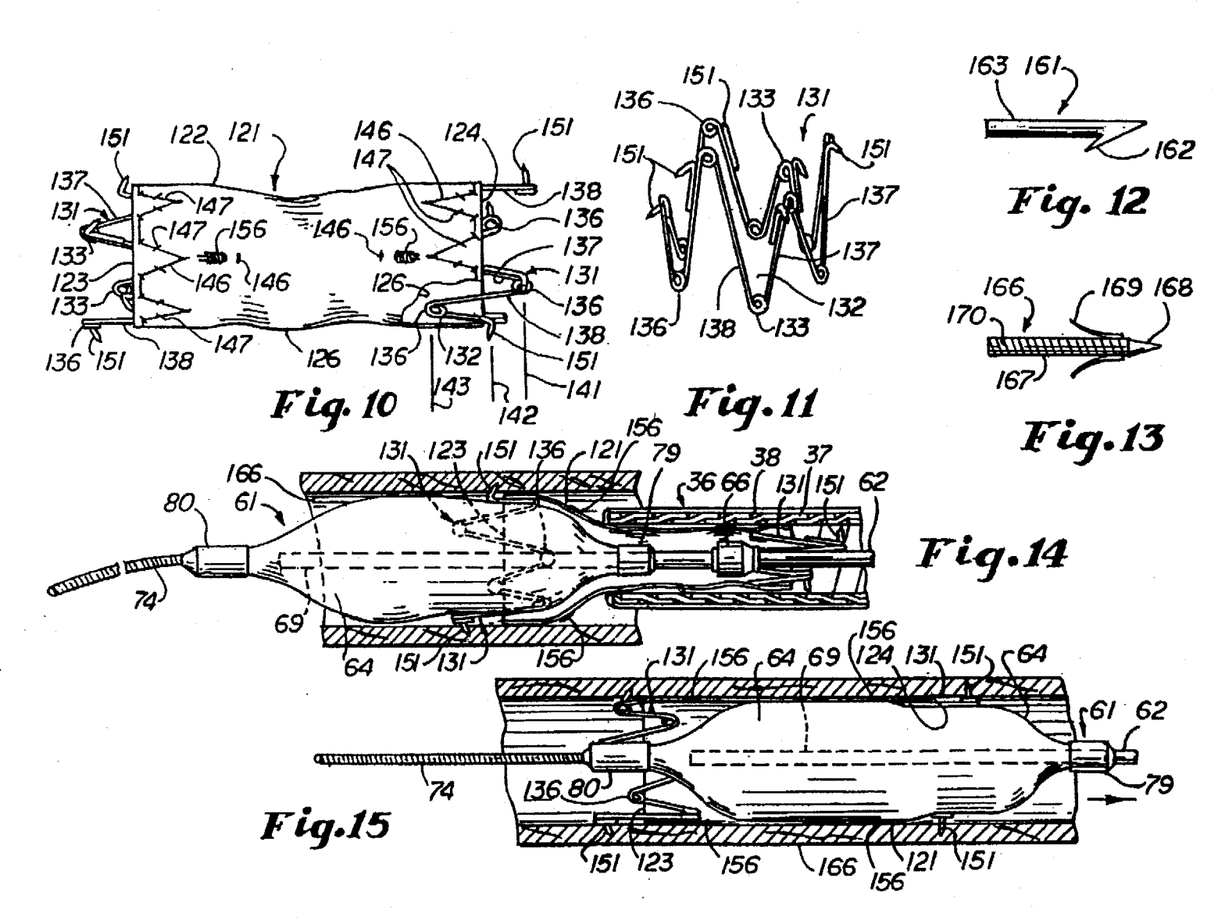
FIG. 10 is a side elevational view of a graft incorporating the present invention.
FIG. 11 is an enlarged isometric view showing one of the spring attachment means utilized on the graft.
FIG. 12 is a partial enlarged view of an alternative hook-like element utilized in the spring attachment means of FIG. 11.
FIG. 13 is an enlarged view showing another embodiment of a hook-like element used in the spring attachment means of FIG. 11.
FIG. 14 is a side elevational view partially in cross section showing the manner in which the graft is held in the capsule after ejection of the proximal extremity of the graft from the capsule.
FIG. 15 is a view similar to FIG. 14 but showing the proximal and distal extremities of the graft outside of the capsule with the balloon retracted so that it is within the graft and inflated to force the distal attachment means into the vessel wall.

The endovascular grafting apparatus 11 also includes an expandable intraluminal vascular graft 121 shown in FIGS. 10 and 11 for implanting in a body vessel. The graft 121 consists of a deformable tubular member 122 which is provided with first and second ends 123 and 124 and a cylindrical or continuous wall 126 extending between the first and second ends 123 and 124. The continuous wall 126 can be woven of any surgical implantable material such as a Dacron-type 56 fiber. One material found to be satisfactory is DeBakey soft woven Dacron vascular prosthesis (uncrimped) sold by USCI. In order to prevent unraveling of the woven material at the ends, the ends can be melted with heat to provide a small melted bead of Dacron on each end. The tubular member 122 can have a suitable length as, for example, 8 to 15 centimeters with 10 centimeters being typical. The tubular member 122 can have a maximum expandable diameter ranging from 14 to 30 millimeters and a minimum diameter in a collapsed condition of 0.175 to 0.300 inches. Expandable spring means 131 is provided on each of the first and second ends 123 and 124 of the tubular member 122 and is secured to the tubular member. The spring means serves to yieldably urge the tubular member 122 from a first compressed or collapsed position to a second expanded position. The spring means 131 is formed of a plurality of vees 132 with the apices 133 of the vees 132 being formed with helical coil springs 136 to yieldably urge the legs 137 and 138 of each of the vees 132 outwardly at a direction at right angles to the plane in which each of the vees lie. The spring means 131 is shown more in detail in FIG. 11 and as shown therein, the spring means is comprised of a single piece of wire which is formed to provide the vees 132 and also to define the helical coil springs 136 between the legs 137 and 138. In the construction shown in FIG. 10, it can be seen that the spring means 131 have apices lying in three longitudinally spaced-apart parallel planes 141, 142 and 143 which are spaced with respect to the longitudinal axis of the tubular member 122. The two ends of the single piece of wire can be welded together in one of the legs 137 and 138 to provide a continuous spring means.

The spring means 131 is secured to the first and second ends 123 and 124 of the tubular member by suitable means such as a Dacron polyester suture material 146 which is utilized for sewing the spring means onto the tubular member. This can be accomplished by a sewing operation with the suture material 146 extending into and out of the wall 126 of the tubular member and in which knots 147 are formed on each of the legs or struts 137 and 138 in such a manner so that the apices lying in the plane 141 extend outwardly and are spaced from the end on which they are mounted and in which the apices lying in the plane 142 extend just beyond the outer edge of the tubular member and in which the apices in the third plane are positioned inwardly from the outer edge.

Hook-like elements 151 are provided on the apices lying in planes 141 and 142 and are secured to the vees 132 in the vicinity of the apices by suitable means such as welding. The hook-like elements 151 can have a suitable diameter such as 0.010 to 0.14 inches and a length from 0.5 to 3 millimeters. The hook-like elements are sharpened to provide conical tips. The hook-like elements 151 should have a length which is sufficient for the hook to penetrate into the vessel wall, but not through the vessel wall.

The spring means 131 with the hook-like elements 151 secured thereto are formed of a corrosion resistant material which has good spring and fatigue characteristics. One such material found to be particularly satisfactory is Elgiloy which is a chromium-cobalt-nickel alloy manufactured and sold by Elgiloy of Elgin, Ill. The wire can have a diameter ranging from 0.010 to 0.015 inches in diameter with the smaller diameter wire being utilized for the smaller diameter tubular members as, for example, 12 to 15 millimeters in diameter and the larger tubular members as, for example, those having a 30 millimeter diameter using the larger wire sizes.

It has been found that the spring force created by the helical coils 136 at the apices 133 is largely determined by the diameter of the wire. The greater the diameter of the wire, the greater the spring force applied to the struts or legs 137 and 138 of the vees. Also, the longer the distances are between the apices lying in planes 141 and 142, the smaller the spring force that is applied to the legs or struts 137 and 138. It therefore has been desirable to provide a spacing between the outer extremities of the legs or struts of approximately one centimeter, although smaller or larger distances may be utilized.

The hook-like elements 151 at the proximal and distal extremities of the graft 121 are angled at suitable angles with respect to longitudinal axis of the tubular member 122. The hook-like elements face towards each other to facilitate holding the graft 121 in place in the vessel of the patient. Thus, the hook-like elements 151 on the proximal extremity 123 are inclined from the longitudinal axis by 55° to 80° and preferably about 65° toward the distal end of the graft 121 in the direction of blood flow. The hook-like elements 151 on the distal end 124 of the graft or implant 121 are inclined from the longitudinal axis by 30° to 90° and preferably 85° in a direction towards the proximal end 123 and opposite the direction of blood flow. The hook-like elements serve as attachment means at each end of the graft 121 and when implanted oppose migration of the graft.

The helical coil springs 136 placed at the nodes or apices 133 of the vees 132 of the spring means 131 serve to facilitate compression of the graft when it is desired to place the same within the capsule 36 as hereinafter described. The compression of the graft is accomplished by deformation of the coil springs 136 within their elastic limits. Placing the nodes or apices 133 in different planes greatly aids in reducing the size to which the graft can be reduced during compression of the same by staggering or offsetting the hooks or hook-like elements 151. This also helps to prevent the hook-like elements from becoming entangled with each other. The natural spring forces of the helical coil springs 136 provided in the apices of the vees serves to expand the graft to its expanded position as soon as the graft is free of the capsule 36. By way of example, as shown in the drawings, three apices or nodes can be provided in the plane 141 and three apices or nodes in the plane 142 which are offset longitudinally with respect to the nodes in plane 141 and six nodes in plane 143. The placement of six nodes or apices 133 in the plane 143 does not interfere with the compression of the graft 151 because there are no hook-like elements 151 at these nodes or apices 133 in the plane. For larger diameter grafts, the spring means 131 can be provided with additional apices or nodes 133 to enhance attachment as hereinafter described.

Radiopaque marker means is carried by the graft 121. The radiopaque marker means takes the form of four radiopaque markers 156. The radiopaque markers are made of a suitable material such as a platinum tungsten alloy wire of a suitable diameter such as 0.003 inches which is wound into a spring coil having a diameter of 0.040 inches and having a length of 0.125 inches. These markers 156 are secured to the tubular member 122 by the same suture material 146. Two of the radiopaque markers 156 are located on the tubular member 122 in spaced apart aligned positions longitudinally of and parallel to the longitudinal axis of the tubular member 122 but are adjacent to the apices 133 lying in the planes 143 at the opposite ends 123 and 124 of the graft 121. Thus the markers 156 are spaced a maximum distance apart on the graft but still within the attachment means carried by the graft 121. Another set of two markers is provided on the tubular member 122 spaced 180° from the first set of two markers along the same longitudinal axis (see FIG. 15). By placing the markers in these positions, it is possible to ascertain the position of the graft 121 and at the same time to ascertain whether or not there has been any twist in the graft between the first and second ends of the graft. In other words when there is no twist in the graft 121 the four markers 156 form four corners of a rectangle. However, if a twist in the graft 121 is present, then the pair of markers 156 at one end of the graft 121 have a different spacing transverse of the longitudinal axis of the graft then the other pair of markers 156 at the other end.

In order to ensure that the graft 121 will not become dislodged after it has been implanted, it may be desirable to provide alternative hook-like elements to ensure that the graft will remain in place after it has been implanted. An alternative hook-like element 161 is shown in FIG. 9 in which each of the hook-like elements 161 has been provided with a barb 162 which extends outwardly from the main body 163 of the hook-like element. Thus by way of example, the main body 163 can be formed of a wire having a suitable diameter such as 0.012 inches with the diameter of the hook-like body in the vicinity of the barb 162 having a suitable diameter such as 0.010 inches. The hook-like element can have a suitable length such as 1.5 millimeters.

Another alternative hook-like element 166 is shown in FIG. 10 which has a body 167 of a suitable diameter extending spring-like ribbons 169 having a suitable dimension such as 0.002 inches in thickness and a width of 0.008 inches are secured by suitable means such as welding to the body 167. As shown, the spring-like elements 169 can flare outwardly so that in the event any attempt is made to withdraw or retract the hook-like element, the spring-like ribbons 169 will become firmly imbedded in the tissue to inhibit such removal. It also should be appreciated that other means can be provided on the hook-like elements to inhibit withdrawal of the same from tissue once they have become embedded in the same. Thus, by way of example as shown in FIG. 13, helical or annular serrations 170 can be provided on the hook body to inhibit such withdrawal. In each of the embodiments with the hook-like elements it can be seen that the profile of the hook-like element is kept to a minimum during the time that it is penetrating the tissue.

The endovascular grafting apparatus 11 is shown assembled for use as shown in FIG. 1 typically in the manner it would be packaged for shipment to a hospital or doctor for use. As shown in FIG. 1, the graft 121 has been compressed or squeezed onto the balloon shaft 62 and is positioned within the capsule 36 with the pusher button 66 being positioned immediately to the rear or proximal to the proximal extremity 123 of the graft 121 (see FIG. 14). In this connection it should be appreciated in order to minimize the diameter of the graft to make use of a capsule of minimum diameter, the balloon catheter should be of minimum profile. The balloon shaft 62 is threaded on the wire 98 and extends into the rigid tube 97 of the pusher rod 96. The balloon 64 is disposed forwardly or distally of the capsule 36. The wire 98 is in engagement with the plug 78 in the distal extremity of the balloon 64.

When it is desired to perform a procedure utilizing an endovascular or system grafting apparatus 11 of the present invention to perform the method of the present invention, an apparatus is selected which has the appropriate size of graft 121 within the capsule 36. The length and size of the graft 121 is determined by the size of the vessel of the patient in which the aneurysm has occurred. Typically the size of the graft 121 is selected so that it has sufficient length to span approximately one centimeter proximal and one centimeter distal of the aneurysm so that the hook-like elements 151 of the graft can seat within normal tissue of the vessel on both sides of the aneurysm. Thus, the graft should be two centimeters longer than the aneurysm being repaired. The diameter is selected by measuring the vessel in a preimplant procedure by conventional radiographic techniques and then using a graft 121 of the next larger one millimeter size. During the preimplant fluoroscopy procedure, using a conventional pigtail catheter, the locations of the renal arteries are ascertained so that they will not be covered by the graft 121 when it is implanted.

Let it be assumed that the patient on whom the operation is to take place has been prepared in a conventional manner by use of a dilator with a guide wire and a sheath (not shown) to open the femoral artery or vessel of the patient. The apparatus 11 is inserted into the sheath which has previously been placed in the femoral artery of the patient. This insertion can be accomplished without a guide wire, with a guide wire or by the use of a soft sheath previously positioned over a guide wire. With the construction shown in FIG. 3, the balloon 64 with its guide wire 74 followed by the capsule 36 is introduced into the femoral artery and advanced in the femoral artery by the physician grasping the proximal extremity of the capsule catheter 12 and the cap of the pusher rod assembly 106. The balloon 64 is twisted into a helix to place it in its helical memory condition to reduce its profile to a minimum. The balloon 64 and the physician 36 are advanced by the physician into the desired position by use of the guide wire 74. The physician slightly rotates the apparatus 11 in the direction of the balloon twist to maintain the helical twist in the balloon 64 and pushes on the apparatus 11.

Typically a desired position will be within the abdominal aorta with the proximal extremity 123 of the graft 121 and at least one centimeter distal to the lower renal artery. At about the same time, the physician should rotate the capsule catheter 12 to rotate the capsule 36 and the graft therein in order to orient the radiopaque graft markers 156 such that the distance between the pair of markers 156 at each end of the graft 121 is maximized. As soon as the capsule 36 is in the desired position, the Touhy Borst O-ring assembly 27 is opened to permit free movement of the pusher rod assembly 96. With the balloon 64 riding well beyond or just distal of the end of the capsule 36, one hand of the physician is used for holding the pusher rod assembly 96 by engaging the cap 101 and holding the pusher rod stationary and pulling outwardly on the capsule catheter 12 with the other hand to cause relative movement between the pusher rod assembly 96 in the inner liner 17 and the capsule 36. This causes the wire 98 of the pusher rod assembly 96 to engage the plug 78 of the balloon catheter assembly 61. The pusher button 66 carried by the balloon catheter shaft 62 which is in engagement with the proximal extremity of the graft 121 in the region of the nodes 133 in the plane 143 forces the graft 121 out of the capsule 36 as the capsule is withdrawn. As soon as the proximal extremity of the graft 121 has cleared the distal extremity of the capsule, the proximal extremity 123 of the graft pops outwardly under the force of the spring means 131 carried by the proximal extremity 123 of the graft and will spring into engagement with the vessel wall 166.

As soon as this has occurred, the pusher rod assembly 96 is pulled out of the capsule catheter 12. While the physician uses one hand to hold the capsule catheter 12 stationary, the catheter shaft 62 which is protruding proximally of the capsule catheter 12 is grasped by the other hand and pulled rearwardly to position the proximal extremity of the balloon 64 into the proximal extremity 123 of the graft 121 as shown in FIG. 15. A conventional hand operated syringe and Touhy Borst adapter (not shown) are then taken and attached to the proximal extremity of the balloon catheter shaft 62. The balloon 64 is then expanded by introducing a suitable gas such as carbon dioxide or a dilute radiopaque liquid from the syringe to urge the hook-like elements 151 outwardly to firmly seat within the vessel wall 166.

As soon as this has been accomplished, the capsule catheter 12 is pulled out further with the balloon 64 still inflated until approximately one-half or more of the graft 121 has cleared the capsule 36. Leaving the balloon inflated provides additional security to ensure that the proximally seated graft 121 will not move during retraction of the capsule 36. The balloon 64 is then deflated. The balloon 64 is then retracted further into the graft and reinflated to ensure that a good attachment is made between the hook-like elements 151 carried by the spring means 131 at the proximal extremity 123 of the graft 121. The capsule 36 can then be removed in successive steps and the balloon deflated, retracted and reinflated. The capsule catheter 12 can then be withdrawn completely to the distal portion of the abdominal aorta to permit the distal extremity 124 of the graft 121 to move out completely of the capsule 36 and to permit its distal extremity 124 to spring open and have the hook-like elements 151 move into engagement with the vessel wall 166. Thereafter, the balloon 64 is again deflated. The balloon catheter shaft is then grasped by the physician's hand and pulled rearwardly to center the balloon 64 within the distal extremity 124 of the graft 121. The balloon 64 is reinflated to set the hook-like elements 151 at the distal extremity of the graft into the vessel wall 166. As soon as this has been completed, the balloon 64 is again deflated. The balloon catheter assembly 61 is then removed from the femoral artery.

The entire procedure hereinbefore can be observed under fluoroscopy. The relative positioning of the graft 121 and the balloon 64 can be readily ascertained by the radiopaque attachment means 131, radiopaque markers 156 provided on the graft, and the radiopaque portions of the balloon 64. If any twisting of the graft 121 has occurred between placement of the proximal hook-like elements and the distal hook-like elements, this can be readily ascertained by observing the four markers 156. Adjustments can be made before ejection of the distal extremity 124 by rotation of the capsule catheter 12 to eliminate any twisting which has occurred. In addition, the distance between the pairs of radiopaque markers 156 longitudinal of the axis is measured on the flat plate abdominal x-ray made during the procedure and compared with the known distance between the pairs of markers 156 longitudinal of the axis of the graft 121 ascertained during manufacture of the graft 121. This is done to ascertain whether longitudinal accordioning of the graft 121 has occurred.

Post implant fluoroscopy procedures can be utilized to confirm the proper implantation of the device by the use of a conventional pigtail catheter. Thereafter the sheath can be removed from the femoral artery and the femoral artery closed with conventional suturing techniques. Tissues should begin to grow into the graft within two to four weeks with tissue completely covering the interior side of the graft within six months so that no portion of the graft thereafter would be in communication with the blood circulating in the vessel. This establishes a complete repair of the aneurysm which had occurred.

It is apparent from the foregoing that there has been provided a new and improved endovascular grafting apparatus, system and method for utilizing the same. The construction of the capsule catheter is such that it has sufficient rigidity to ensure easy and ready placement of the capsule carried thereby. The pusher rod assembly which is used therein is constrained in such a manner so that relatively great forces can be applied to the pusher rod assembly even though the pusher wire has only a diameter of 0.018 inches. The tube 69 also serves to provide a confined space for the wire 98 to sit in while a high compressive force is being applied to the wire. The tube 69 prevents the wire from buckling or kinking within the balloon. It also prevents the balloon from collapsing during insertion of the apparatus 11. The capsule 36 which is provided as a part of the catheter assembly is formed of metal which makes it possible to utilize grafts having very sharp hook-like elements without any danger of them penetrating the capsule during the time that the capsule is being introduced into the vessel of the patient. In addition, the capsule since it is flexible and can bend through angles up to approximately 120° in order to readily negotiate the bends which occur in the vessel of the patient. The balloon catheter is made in such a way that the balloon can be readily introduced into the vessel because of the rigid tubular member provided within the balloon while at the same time permitting inflation and deflation of the balloon through the same tubular member. The pusher button 66 is mounted on the balloon catheter in such a manner so that it cannot shift at all in one direction or proximally longitudinally of the balloon catheter. The pusher button 66 also can only move a limited distance towards the balloon 64 until it reaches the balloon 64. In one embodiment shown in FIG. 3 the pusher button 66 cannot move proximally or distally whereas in another embodiment shown in FIG. 4 it cannot move proximally but can move distally. This is an advantage when retracting the proximal extremity of the balloon 64 into the graft 121 for placement of the proximal hook-like elements 151 because the pusher button 66 can slide forwardly or distally of the shaft 62 as the shaft 62 is retracted to bring the proximal extremity with the balloon 64 into the graft 121. Thus the pusher button 66 will not be pulled back into the capsule 36 and catch on the collapsed distal extremity 124 of the graft 121 within the capsule 36. The balloon is also mounted on the distal extremity of the balloon catheter in such a manner so that the balloon cannot leak. The balloon catheter can be provided with either a fixed guide wire, or if desired, a movable guide wire so that an over-the-wire system can be utilized.

The capsule 36 is constructed in such a manner so that it is semi-radiopaque allowing it to be visualized while still permitting observation of the graft within the capsule and the attachment means provided on the graft. The capsule 36 is also constructed in such a manner so that the hooks which are provided on the graft will readily slide in one direction over the wraps or turns of the capsule without hanging up or catching onto the individual wraps of the ribbon forming the capsule.

The graft which is provided with the helical coil springs at each of the nodes is particularly advantageous in that it permits compression of the graft into a very small size without causing permanent deformation of the attachment means. Because of the spring forces provided by the attachment means, it is possible that the grafts can be implanted without the use of an inflatable balloon for forcing the hook-like elements into the tissue of the vessel. However, at the present time, it is still believed to be desirable to utilize the balloon to ensure that the hook-like elements are firmly implanted into the wall of the vessel so as to inhibit migration of the graft within the vessel.

What is claimed is:

1. An endovascular grafting system for intraluminal emplacement of a prosthesis in a corporeal lumen, comprising:

a prosthesis configured to repair the corporeal lumen; and a catheter having an inflatable portion, said catheter being operatively associated with said prosthesis for intraluminally deploying said prosthesis within the corporeal lumen, said inflatable portion configured to engage said prosthesis to implant said prosthesis within the corporeal lumen so that said prosthesis repairs the corporeal lumen.

2. The medical system of claim 1, further comprising means in operative relationship with said prosthesis and said catheter for fastening said prosthesis within a corporeal lumen.

3. The medical system of claim 2, wherein said prosthesis is a hollow graft capable of being fastened in an aorta by said means for fastening to intraluminally repair the aorta.

4. The medical system of claim 1, wherein said prosthesis comprises a hollow tubular graft having a proximal portion and having means proximate to said proximal portion for fastening said proximal portion within a corporeal lumen.

5. The medical system of claim 4, wherein said means for fastening comprises an intraluminal fastening device connected to said proximal portion, said fastening device having a plurality of staples capable of engaging a corporeal lumen in which said prosthesis is emplaced to fasten said prosthesis therein.

6. The medical system of claim 5, further comprising an inflation device, wherein said inflatable portion can be inflated by said inflation device to cause said staples to engage the lumen, and can be deflated by said inflation device to disassociate said catheter from the fastened said prosthesis.

7. An endovascular grafting system for intraluminal emplacement of a prosthesis in a corporeal lumen, comprising:

a prosthesis configured to repair the corporeal lumen, said prosthesis having a collapsed condition for intraluminal delivery and an expanded condition for prosthetic use; and a catheter having an inflatable portion, said catheter being operatively associated with said prosthesis, wherein said catheter is configured to carry said prosthesis in said collapsed condition to a desired position within the lumen and said inflatable portion is configured to engage said prosthesis and to expand said prosthesis to said expanded condition in order to implant said prosthesis within the corporeal lumen so that said prosthesis repairs the corporeal lumen.

8. The medical system of claim 7, further comprising an intraluminal fastening device in operative relationship with said prosthesis and said catheter.

9. The medical system of claim 8, wherein:

said prosthesis comprises a flexible, hollow graft having a tubular shape;

said graft has a proximal end portion for placement upstream in a fluid conducting corporeal lumen; and said fastening device is positioned proximate said proximal end portion, wherein said catheter is capable of emplacing said graft at a desired position in a damaged or diseased fluid conducting corporeal lumen to repair or reinforce the corporeal lumen.

10. The medical system of claim 9, wherein said fastening device comprises staples capable of engaging an inner wall of a corporeal lumen into which said graft is emplaced, and said graft is made of a deformable material having a high tissue ingrowth rate, said graft being deformable both axially and radially and capable of substantially conforming to an interior shape of a corporeal lumen into which said graft is emplaced.

11. An endovascular grafting system for intraluminal emplacement of a prosthesis in a corporeal lumen, comprising:

a prosthesis configured to repair the corporeal lumen, said prosthesis having a collapsed condition for intraluminal delivery and an expanded condition for prosthetic use; and a catheter having an inflatable portion with said prosthesis disposed thereon, said inflatable portion being selectively inflatable to engage said prosthesis and to expand said prosthesis from said collapsed condition to said expanded condition in order to implant said prosthesis within the corporeal lumen so that said prosthesis repairs the corporeal lumen.

12. The medical system of claim 11, further comprising an intraluminal fastening device in operative relationship with said prosthesis and said catheter, and inflation means for inflating and deflating said inflatable portion.

13. The medical system of claim 12, wherein said prosthesis is an elongated, hollow graft having a first end portion, and said fastening device is in operative relationship with said first end portion such that said inflatable portion can be inflated by said inflation means to operate said fastening device to fasten said graft within a corporeal lumen.

14. The medical system of claim 13, wherein said fastening device comprises staples connected to said first end portion, said staples being capable of engaging an inner wall of a corporeal lumen.

15. An endovascular grafting system for intraluminal emplacement of a prosthesis in a corporeal lumen, comprising:

an elongated tubular prosthesis having opposite end portions in fluid communication with one another for use in repairing an aortic aneurysm, said prosthesis having a collapsed condition for intraluminal delivery and an expanded condition for prosthetic use; and a catheter having an inflatable portion, said catheter being operatively associated with said prosthesis, said inflatable portion being inflatable to engage said prosthesis and to expand said prosthesis from said collapsed condition to said expanded condition to thereby implant said prosthesis within the corporeal lumen so that said prosthesis repairs the corporeal lumen, said inflatable portion being deflatable to enable disassociation of said catheter from said prosthesis.

16. The medical system of claim 15, further comprising an intraluminal fastening device at one end portion of said prosthesis.

17. The medical system of claim 16, wherein said inflatable portion can inflate to cause said fastening device to fasten said one end portion within a lumen, and can deflate to disassociate said catheter from said prosthesis.

18. The medical system of claim 16, wherein said fastening device comprises a plurality of staples.

19. A method for intraluminal emplacement of a prosthesis in a corporeal lumen, comprising the step of:

intraluminally emplacing a prosthesis configured to repair the corporeal lumen in the corporeal lumen using a catheter having an inflatable portion, said inflatable portion engaging and expanding said prosthesis during said emplacing step to thereby implant said prosthesis in the corporeal lumen so that said prosthesis repair the corporeal lumen, said prosthesis being disassociated from said catheter and inflatable portion after said emplacing step.

20. The method of claim 19, wherein said prosthesis has a collapsed condition and an expanded condition, and said emplacing step includes the steps of:

making an opening in said corporeal lumen;

inserting said prosthesis in said collapsed condition and said inflatable portion of said catheter into said lumen through said opening to a desired position in said lumen;

inflating said inflatable portion to expand said prosthesis to said expanded condition; and deflating said inflatable portion to disassociate said catheter from said prosthesis.

21. The method of claim 20, wherein said prosthesis is a hollow tubular graft having first and second end portions in fluid communication, said first end portion having an intraluminal fastening device in operative association therewith;

wherein said first end portion of said graft is emplaced upstream in said lumen, and said inflation step causes said fastening device to fasten said first end portion within said lumen.

22. The method of claim 21, wherein said fastening device comprises staples connected to said first end portion of said graft, wherein said inflatable portion is inflated in said fastening device to force said staples to penetrate said lumen.

23. The method of claim 22, wherein said graft is positioned to span an aortic aneurysm to repair or reinforce a length of said aneurysm, said graft being selected to have a length equal to or greater than the length of said aortic aneurysm.

24. A method for intraluminally implanting a prosthesis at a desired location within a corporeal lumen comprising the steps of:

disposing a prosthesis configured to repair the corporeal lumen upon a catheter;

intraluminally inserting said prosthesis and catheter within a corporeal lumen;

delivering said catheter and prosthesis through the corporeal lumen to a desired location in the corporeal lumen without surgically exposing the desired location of the corporeal lumen; and providing controllable expansion of said prosthesis at the desired location within the corporeal lumen by expanding an inflatable portion of said catheter associated with said prosthesis to engage said prosthesis and force said prosthesis radially outwardly to implant said prosthesis within the corporeal lumen to configure said prosthesis so that the corporeal lumen is repaired.

* * * * *

UNITED STATES PATENT AND TRADEMARK OFFICE
CERTIFICATE OF CORRECTION

PATENT NO.    : 5,669,936
DATED         : Sep. 23, 1997
INVENTOR(S)   : Harrison Lazarus It is certified that error appears in the above-identified patent and that said Letters Patent is hereby corrected as shown below:

Cover page, Under "Related U.S. Application Dates, Last line, Change "Dec. 9, 1993", To read --Dec. 9, 1983--.

Cover page, Replace figure with "FIG.1" on drawings "Sheet 1 Of 5", hereon attached.

In the drawings, Replace "Sheet 1 of 5", with --Sheet 1 of 5--, hereon attached.

In the drawings, Replace "Sheet 3 of 5", with --Sheet 3 of 5--, hereon attached.

Column 2, Line 58, After "0.187", add a space.

Column 2, Line 58, After "of", add a space.

Column 2, Line 63, After "sulfate.", add two spaces.

Column 16, Claim 24, Line 57, After "and", add --to--.

Signed and Sealed this

Seventh Day of April, 1998

Attest:

BRUCE LEHMAN

*Attesting Officer*    *Commissioner of Patents and Trademarks*

United States Patent
Lazarus

Patent Number: 5,669,936
Date of Patent: *Sep. 23, 1997

[54] ENDOVASCULAR GRAFTING SYSTEM AND METHOD FOR USE THEREWITH

[75] Inventor: Harrison M. Lazarus, Salt Lake City, Utah

[73] Assignee: Endovascular Technologies, Inc., Menlo Park, Calif.

[*] Notice: The term of this patent shall not extend beyond the expiration date of Pat. No. 4,787,899.

[21] Appl. No.: 395,157

[22] Filed: Feb. 27, 1995

Related U.S. Application Data

[63] Continuation of Ser. No. 103,442, Aug. 6, 1993, abandoned, which is a continuation of Ser. No. 553,530, Jul. 13, 1990, Pat. No. 5,275,622, which is a continuation-in-part of Ser. No. 166,093, Mar. 9, 1988, Pat. No. 5,104,399, which is a continuation-in-part of Ser. No. 940,907, Dec. 10, 1986, Pat. No. 4,787,899, which is a continuation of Ser. No. 559,935, Dec. 9, 1983, abandoned.

[51] Int. Cl.$^6$ .................. A61F 2/06; A61M 29/00
[52] U.S. Cl. .................. 623/1; 623/12; 606/195
[58] Field of Search .................. 623/1, 11, 12; 604/96; 606/191–198

[56] References Cited

U.S. PATENT DOCUMENTS

| | | | |
|---|---|---|---|
| 3,878,565 | 4/1975 | Sauvage | 623/1 |
| 3,882,852 | 5/1975 | Sinnreich | 604/96 X |
| 3,890,976 | 6/1975 | Bazell et al. | 604/96 X |
| 4,140,126 | 2/1979 | Choudhury | 623/1 |
| 4,141,364 | 2/1979 | Schultze | 604/96 |
| 4,276,874 | 7/1981 | Wolvek et al. | 604/96 |
| 4,560,374 | 12/1985 | Hammerslag | 604/49 |
| 4,655,771 | 4/1987 | Wallstén | 623/1 |
| 4,787,899 | 11/1988 | Lazarus | 623/1 |
| 4,954,126 | 9/1990 | Wallstén | 623/1 X |
| 5,104,399 | 4/1992 | Lazarus | 623/1 |

FOREIGN PATENT DOCUMENTS

| | | |
|---|---|---|
| 1217402 A | 3/1986 | U.S.S.R. |
| 4318235 A1 | 6/1987 | U.S.S.R. |
| 1389778 A2 | 4/1988 | U.S.S.R. |
| 1457921 A1 | 2/1989 | U.S.S.R. |
| 1482714 A2 | 5/1989 | U.S.S.R. |

Primary Examiner—Debra S. Brittingham
Attorney, Agent, or Firm—Fulwider Patton Lee & Utecht

[57] ABSTRACT

Endovascular grafting system having a capsule catheter comprising a flexible elongate tubular member having proximal and distal extremities and a capsule mounted on the distal extremity of the tubular member. The capsule is generally cylindrical in shape and is formed of a helical wrap of a metal ribbon. The wraps are bonded into a unitary capsule permitting bending of said unitary capsule. A graft is disposed within the capsule. The graft is comprised of a tubular member having proximal and distal ends. Hooks are secured to the proximal and distal ends of the tubular member and face in a direction outwardly towards the inner wall of the capsule. A push rod is disposed within the capsule catheter and engages the graft whereby upon relative movement between the push rod and the capsule catheter, the graft can be forced out of the capsule.

24 Claims, 5 Drawing Sheets

FIG. 1